United States Patent
Van Hal et al.

(10) Patent No.: US 7,252,628 B2
(45) Date of Patent: Aug. 7, 2007

(54) DEVICE FOR TREATING HUMAN SKIN BY MEANS OF RADIATION

(75) Inventors: Robbert Adrianus Maria Van Hal, Eindhoven (NL); Bernardus Leonardus Gerardus Bakker, Eindhoven (NL); Michiel Errit Roersma, Eindhoven (NL); Peter Bjerring, Risskov (DK)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/538,620

(22) PCT Filed: Nov. 18, 2003

(86) PCT No.: PCT/IB03/05263

§ 371 (c)(1),
(2), (4) Date: Mar. 14, 2006

(87) PCT Pub. No.: WO2004/054458

PCT Pub. Date: Jul. 1, 2004

(65) Prior Publication Data

US 2006/0217586 A1    Sep. 28, 2006

(30) Foreign Application Priority Data

Dec. 18, 2002    (EP) .................... 02080361

(51) Int. Cl.
*A61N 5/00* (2006.01)
(52) U.S. Cl. .............................. 600/1; 606/9

(58) Field of Classification Search ................ 600/1–8; 606/9
See application file for complete search history.

(56) References Cited

U.S. PATENT DOCUMENTS 4,503,327 A * 3/1985 Wilson ........................ 250/261
2002/0173780 A1* 11/2002 Altshuler et al. .............. 606/9

* cited by examiner

*Primary Examiner*—John P. Lacyk
(74) *Attorney, Agent, or Firm*—Adam L. Stroud

(57) ABSTRACT

The invention relates to a device (1) for treating human skin by means of radiation. The device has a housing (5) with a radiation exit opening (13), a radiation source (9) which is accommodated in the housing, and a radiation path (15) between the radiation source and the radiation exit opening. A radiation filter (17) is provided in the radiation path. According to the invention the radiation filter (17) comprises water (23) which is in solid state at least during an initial phase of operation of the device (1). The water in solid state has an optical transmission spectrum which corresponds to the optical transmission spectrum of water in liquid state as present in the skin. As a result the water in solid state acts as an ideal filter for the IR light and near IR light, which would otherwise be absorbed by the water in the skin and cause unwanted heating of the skin. An additional advantage of the water in solid state is its relatively high heat absorbing capacity and its ability to cool the skin in case of direct thermal contact with the skin. In a particular embodiment the device (1) is an epilator for the removal of hairs from the human skin, the radiation source (9) being a flash lamp which generates light pulses having a high energy density and a broad optical spectrum.

16 Claims, 3 Drawing Sheets

DEVICE FOR TREATING HUMAN SKIN BY MEANS OF RADIATION

Figure 1:
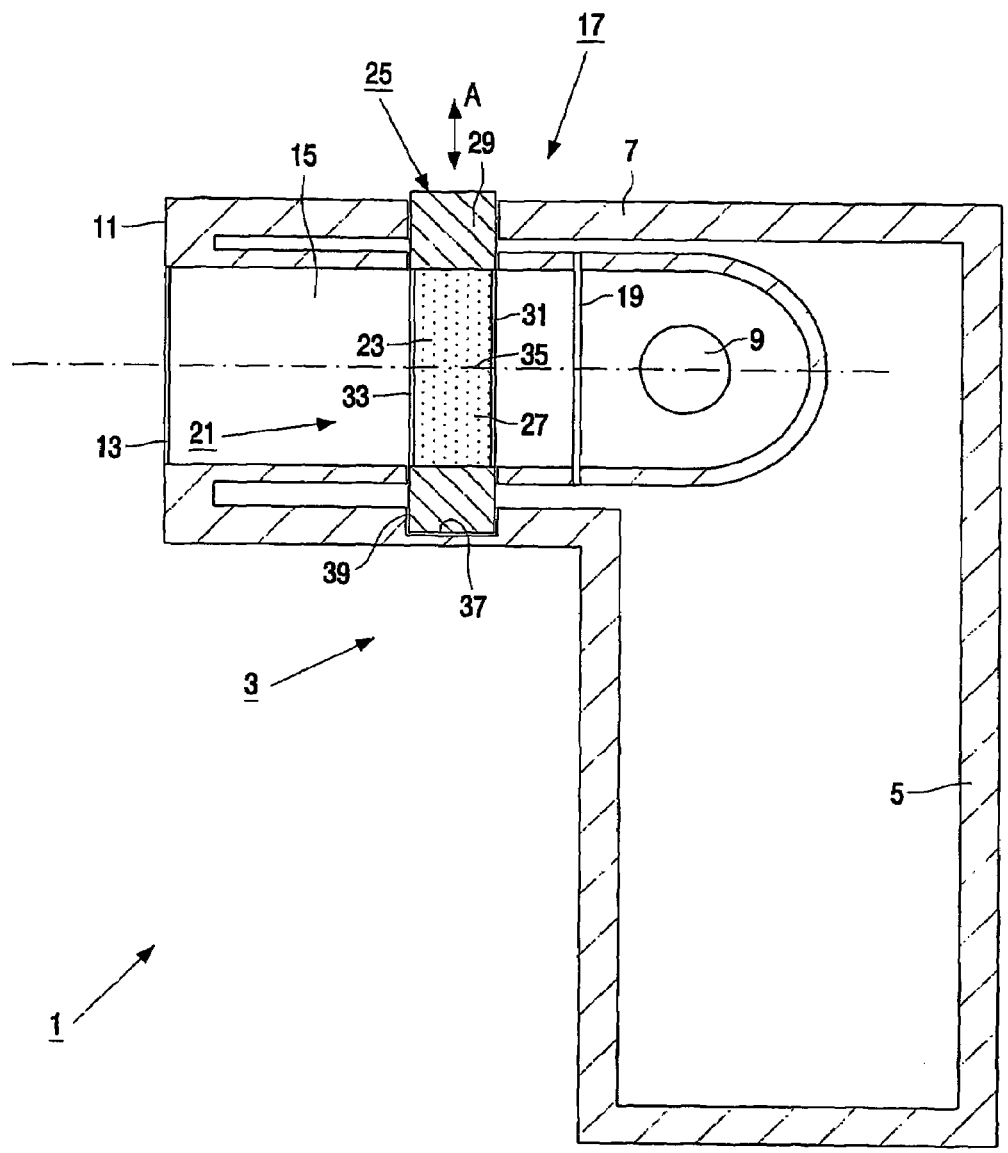

The invention relates to a device for treating human skin by means of radiation, which device comprises a housing, a radiation source accommodated in the housing, a radiation exit opening, a radiation path between the radiation source and the radiation exit opening, and a radiation filter positioned in the radiation path and comprising water.

The invention further relates to a holder for water in solid state for use in a device for treating human skin in accordance with the invention.

A device for treating human skin of the kind mentioned in the opening paragraph is known from EP-A-0 885 629. The known device is a device for therapeutic or cosmetic phototreatment of human skin. The radiation source of the known device is a flash lamp which is arranged in a chamber. Said chamber is enclosed by a reflector and by a long wave pass filter and is filled with water in liquid state. The chamber comprises a first portion of the radiation path of the known device. The radiation path further comprises a tubular light guide which extends from the long wave pass filter until the radiation exit opening. The long wave pass filter is adapted to absorb a portion of the light generated by the flash lamp in the UV range and near UV range. The water in the chamber cools the lamp. The water further acts as a radiation filter for absorbing the infra-red portion of the light generated by the flash lamp. Without such a radiation filter excessive heating of the human skin would be caused during operation due to the fact that the water present in the human skin would absorb the infra-red light which is present in the light of the flash lamp. Since the radiation filter of the known device comprises water, the radiation filter effectively absorbs the infra-red light which would otherwise be absorbed by the water in the human skin, so that said radiation filter acts as an ideal infra-red filter.

In a first embodiment disclosed in EP-A-0 885 629 the water is circulated over the flash lamp and through the chamber, so that the heat generated in the water by the flash lamp and generated as a result of absorption of the infra-red light is continuously transported away from the chamber to a heat exchanger arranged externally of the device. A disadvantage of the first embodiment is that the device has a complex structure as a result of the need of a closed circuit for the water comprising a pump and a heat exchanger. In a second embodiment disclosed in EP-A-0 885 629 the water does not cool the flash lamp but is contained in a transparent vessel so as to act purely as an infra-red filter. A disadvantage of the second embodiment however is that the water is heated as a result of the absorption of the infra-red light, so that in order to avoid excessive heating of the water either a comparatively large amount of water should be used, which adversely effects the dimensions and weight of the device, or the time period during which the device can be operated without interruption is limited.

It is an object of the invention to provide a device for treating human skin of the kind mentioned in the opening paragraph in which the disadvantages of the known device described before are prevented as much as possible.

In order to achieve said object, a device for treating human skin in accordance with the invention is characterized in that at least during an initial phase of operation of the device the radiation filter comprises water in solid state. Experiments have shown that water in solid state has an optical transmission spectrum which is comparable to the optical transmission spectrum of water in liquid state. As a result the radiation filter of the device in accordance with the invention acts as an effective filter for infra-red radiation in a manner comparable to the radiation filter of the known device comprising water in liquid state. However since the radiation filter of the device in accordance with the invention comprises water in solid state at least during an initial phase of operation of the device, the radiation filter has a significantly higher heat absorbing capacity than the radiation filter of the known device when a comparable amount of water is used. Said higher heat absorbing capacity is not only caused by the fact that water in solid state has a much lower temperature than water in liquid state, so that more heat can be absorbed by the water before a predetermined allowable temperature limit of the water is reached, but is also caused by the fact that an additional amount of heat can be absorbed by the water when passing from the solid state into the liquid state. As a result a sufficient heat absorbing capacity of the radiation filter, allowing a sufficient period of operation without interruption, is obtained without the need of an additional cooling circuit with a pump and a heat exchanger and without the need of an excessive amount of water.

A particular embodiment of a device for treating human skin in accordance with the invention is characterized in that during operation the water in solid state is in thermal contact with the skin to be treated. Since during operation the water in solid state is in thermal contact with the skin, the water in solid state does not only have a filtering function for the radiation generated by the radiation source, but also has a cooling function for the skin to be treated. Despite the filtering function of the water in solid state, the skin to be treated is still heated as a result of the absorption of the portions of the radiation which are transmitted by the radiation filter and by means of which the skin is treated. The cooling function of the water in solid state does not only limit or prevent heating of the skin, but also provides a pain masking effect.

A particular embodiment of a device for treating human skin in accordance with the invention is characterized in that the device comprises a releasable and removable holder for the water in solid state. After use of the device, the holder can be released and removed from the device and can be placed in a freezer in order to decrease the temperature of the water in solid state present in the holder and/or to freeze the water in the holder in case it was melted during use of the device. After this, the holder can be placed back in the device, and the device is ready for a next operation. In this manner the device does not need to comprise a cooling system to maintain the water in solid state at a prescribed temperature.

A further embodiment of a device for treating human skin in accordance with the invention is characterized in that the holder comprises a transparent material having a predetermined optical transmission spectrum such that said material substantially transmits radiation having a wavelength above a predetermined threshold value and substantially reflects or absorbs radiation having a wavelength below said threshold value. As mentioned before the water in solid state functions as a radiation filter for infra-red light, said filter substantially transmitting radiation having a wavelength below approximately 950 nm and substantially absorbing radiation having a wavelength above approximately 950 nm. For a large number of skin treatments, however, the radiation below a predetermined threshold value, e.g. below approximately 500 nm or 600 nm, is not effective for the skin treatment and only causes injuries or other unwanted side effects of the skin. In this further embodiment said material of the holder, in which the water in solid state is contained, is used as an additional radiation filter which limits or prevents the transmission of radiation having wavelengths below said predetermined threshold value. In view of this double function the holder is used in a practical manner, and said injuries or other unwanted side effects on the skin are limited or prevented.

A particular embodiment of a device for treating human skin in accordance with the invention is characterized in that the device comprises a cooling device for cooling the water in solid state. In this embodiment the water in solid state is held at a substantially constant temperature or the rate of increase of the temperature of the water in solid state is limited by said cooling device, so that the device can be used for a much longer time without interruption or can even be used continuously. Said cooling device can be of a relatively simple kind, such as for example a thermo-electric cooler forming part of the device. In such an embodiment, the use of a freezer is not necessary. In another example the cooling device comprises a compound having a eutectic composition with a eutectic temperature substantially lower than the melting temperature of the water. Said compound is held in an additional holder in thermal contact with the holder holding the water in solid state. During operation, when said compound reaches its eutectic temperature, said compound passes from the solid state into the liquid state at a substantially constant temperature. During this the water in solid state is maintained at a substantially constant temperature below its melting temperature as a result of the thermal contact between the holder and the additional holder. After use the holder containing the water and the additional holder containing said compound can be placed together in a freezer to bring both the water and said compound back to their solid states.

A particular embodiment of a device for treating human skin in accordance with the invention is characterized in that during operation the water in solid state is in direct contact with the skin to be treated. In this embodiment a thin water film is formed during operation between the water in solid state present near the radiation exit opening and the skin, because a small portion of the water in solid state will melt as a result of the direct contact with the skin. As a result of said water film scattering and reflection of the radiation at the surface of the skin is limited, and a larger portion of the radiation is effectively transmitted into the skin via the water film. Said improved transmission is a result of the fact that a good optical contact is present between the water in solid state and the water film and between the water film and the surface of the skin, and also of the fact that the water film has a refraction coefficient which is closer to the refraction coefficient of the skin than the refraction coefficient of air.

A particular embodiment of a device for treating human skin in accordance with the invention is characterized in that the water in solid state comprises an additive. The application of an additive in the water in solid state can have various purposes and advantages. In an embodiment in which the water in solid state is in direct contact with the skin, said additive will be applied to the skin when a portion of the water in solid state melts on the skin. In such an embodiment the additive may have a skin-treating function, such as a skin hydrating, a skin de-sensitizing, or a skin irritation reducing function. Furthermore in such an embodiment, and also in embodiments in which the water in solid state is not in direct contact with the skin, additives may be applied to the water in solid state which, for example, increase the radiation absorbing capacity of the water in solid state for wavelengths which are not effective for the treatment of the skin and are harmful for the skin.

A particular embodiment of a device for treating human skin in accordance with the invention is characterized in that the device is a device for removing hairs from human skin, wherein the radiation source is a flash lamp. The light of the flash lamp has a relatively broad spectrum ranging from UV light to near IR light. The portion of this spectrum which is effective for the removal of hairs from human skin lies between approximately 600 nm and 900 nm. The portions of this spectrum below approximately 600 nm and above approximately 900 nm are not effective for the removal of hairs and in addition cause unwanted side effects on the skin such as excessive heating of the skin or even DNA mutations. The energy density of the light necessary to remove the hairs is relatively high, so that the radiation filter has to absorb a large amount of energy. In view of these properties of the light of the flash lamp, the invention is particularly suitable for use in a device for removing hairs by means of a flash lamp, at least for effectively filtering the portions of the light having wavelengths above approximately 900 nm.

In accordance with the invention, a holder for water in solid state for use in a device for treating human skin in accordance with the invention is characterized in that the holder comprises a chamber for containing water in solid state, said chamber comprising an optically transparent radiation path which, during operation, extends through the water in solid state, and said holder comprising positioning means which are arranged outside said radiation path and which define a predetermined position of said radiation path in the device.

A particular embodiment of a holder for water in solid state in accordance with the invention is characterized in that the holder comprises an additional chamber which is in thermal contact with the chamber for containing the water in solid state and which comprises a compound having a eutectic composition with a eutectic temperature lower than the melting temperature of the water in solid state.

Figure 2:
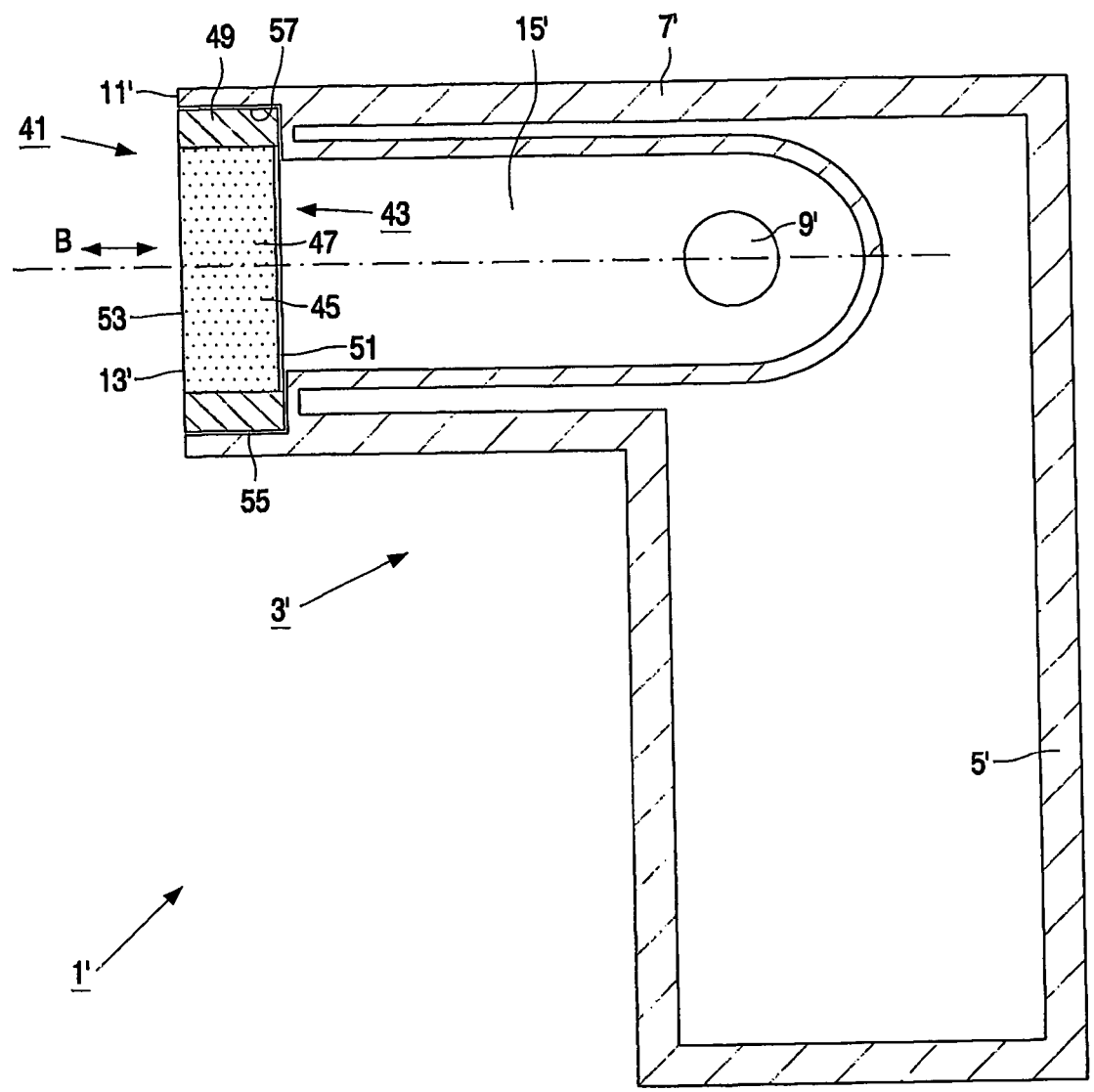
Figure 3:
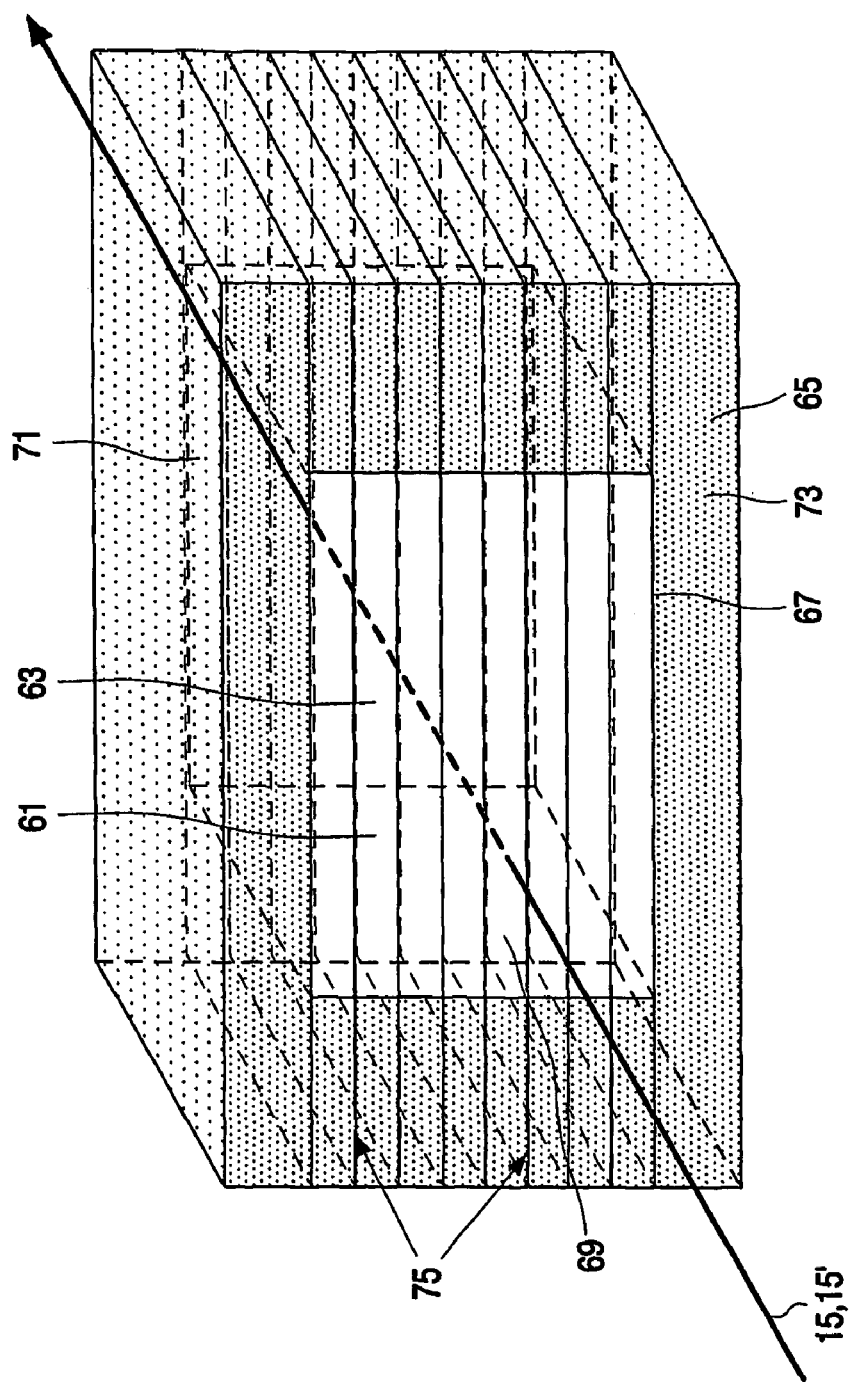

In the following, embodiments of a device for treating human skin in accordance with the invention will be described with reference to the figures, in which FIG. 1 schematically shows a first embodiment of a device for treating human skin in accordance with the invention, FIG. 2 schematically shows a second embodiment of a device for treating human skin in accordance with the invention, and FIG. 3 schematically shows a releasable and removable holder for water in solid state for use in the devices of FIG. 1 and FIG. 2.

The first embodiment of a device 1 for treating human skin in accordance with the invention is a device for removing hairs from human skin, in particular an epilator for removing the hairs for a relatively long time or even permanently. FIG. 1 schematically shows only the main parts of the device 1 which are necessary to understand the principles of the invention. The device 1 comprises a housing 3 having a grip 5 and a head 7 mounted on the grip 5. The head 7 accommodates a radiation source 9, which is a gas filled linear flash lamp in this particular embodiment. In a front portion 11 of the head 7 a radiation exit opening 13 is provided for the light generated during operation by the radiation source 9. The head 7 further accommodates a radiation path 15, which extends between the radiation source 9 and the radiation exit opening 13. During operation the radiation source 9 generates light pulses having a relatively high energy density, which propagate from the radiation source 9 towards the radiation exit opening 13 and irradiate the human skin present in front of the radiation exit opening 13. Part of the light is absorbed by the hair roots and the hair follicles present in the skin, which are considerably heated as a result of the relatively high energy density of the light. As a result the hair roots and the hair follicles are damaged or even destroyed, so that growing of the hairs is prevented for a considerably long time or even permanently.

The light generated by the radiation source 9 has a relatively broad spectrum ranging from UV light to near IR light and IR light. Of this spectrum only the portion of the light having a wavelength between approximately 600 nm and approximately 900 nm is effective for the removal of the hairs. The portions of the light having a wavelength below approximately 600 nm and above approximately 900 nm are not effective for the removal of the hairs and cause unwanted side effects on the skin. The portion of the light having a wavelength below approximately 600 nm, in particular the UV light, may lead to skin injuries and even to DNA mutations. The portion of the light having a wavelength above approximately 900 nm, in particular the near IR light and IR light, leads to excessive heating of the skin, which is caused by the fact that the near IR light and IR light is strongly absorbed by the water present in the skin. In order to limit or even prevent such unwanted side effects on the skin, the device 1 comprises a radiation filter 17 which is positioned in the radiation path 15 between the radiation source 9 and the radiation exit opening 13 in order to limit or prevent the transmission of said non-effective and harmful portions of the light to the skin.

In the embodiment of FIG. 1 the radiation filter 17 comprises a first filter portion 19 and a second filter portion 21. The first filter portion 19 is a long wave pass filter and comprises a heat resistant glass filter having a suitable coating or filler material such that the first filter portion 19 substantially absorbs or reflects portions of the light having a wavelength below approximately 600 nm. A person skilled in the art will be able to find any commercially available glass filter suitable for this purpose. According to the invention, the second filter portion 21 comprises water in solid state 23 at least during an initial phase of operation of the device 1, wherein the light transmitted by the first filter portion 19 passes through the water in solid state 23 towards the radiation exit opening 13. As discussed before the portions of the light of the radiation source 9 having a wavelength above approximately 900 nm would cause excessive heating of the skin as a result of the fact that said portions of the light are strongly absorbed by the water present in the skin. The water in solid state 23 present in the second filter portion 21 has an optical transmission spectrum which substantially corresponds to the optical transmission spectrum of the liquid water present in the skin. As a result, the second filter portion 21 effectively absorbs the portions of the light, in particular the near IR light and the IR light, which would be absorbed by the water in the skin in the absence of the second filter portion 21. As a result the second filter portion 21 comprising the water in solid state 23 acts as an ideal IR filter, which effectively limits or even prevents heating of the skin by the near IR light and the IR light.

An additional advantage of the use of the water in solid state 23 in the second filter portion 21 is that the second filter portion 21 has a comparatively high heat absorbing capacity. Said high heat absorbing capacity is caused by the fact that the water in solid state 23 has a comparatively low temperature, so that a comparatively large amount of heat can be absorbed by the second filter portion 21 before a prescribed temperature limit of the second filter portion 21 is reached. In addition the heat absorbing capacity of the second filter portion 21 is further increased as the water in solid state 23 is allowed to melt during operation. When passing from the solid into the liquid state, the water remains at a substantially constant temperature, while a significant amount of heat (melting energy) is absorbed. As a result of the comparatively high heat absorbing capacity of the second filter portion 21, the device 1 can be used for a comparatively long period of time without interruption, while the necessary mass and volume of the water in solid state 23 in the second filter portion 21 is limited.

In the device 1 shown in FIG. 1 the water in solid state 23 is held in a holder 25 which is releasable and removable from the device 1 in the direction of the arrow A in FIG. 1. The holder 25 comprises a chamber 27 for containing the water in solid state 23. The chamber 27 is enclosed by an annular carrier 29, by a first optically transparent cover plate 31, and by a second optically transparent cover plate 33, said cover plates 31, 33 being made from, for example, glass or sapphire. Thus the chamber 27 has an optically transparent radiation path 35, which extends through the water in solid state 23 and comprises the cover plates 31, 33 as well as the portion of the chamber 27 present between the cover plates 31, 33. The holder 25 further comprises positioning means 37, which are arranged outside the radiation path 35 of the chamber 27 and which define a predetermined position of said radiation path 35 and of the water in solid state 23 in the device 1. In the embodiment shown in FIG. 1 said positioning means 37 are formed by a circumferential edge portion of the annular carrier 29, which matches a recess 39 provided in the head 7 of the device 1. When said edge portion is placed in a correct position in the recess 39, a major portion of the water in solid state 23 is present in the radiation path 15 of the device 1. After use of the device 1, when the water in solid state 23 is melted and heated as a result of the absorption of the IR and near IR light, the holder 25 can be released and removed from the device 1 and can be placed in a freezer in order to freeze the water in the holder 25 again and to further decrease the temperature of the water in solid state 23. Before the next use of the device 1, the holder 25 is to be replaced in the recess 39, after which the device 1 is ready for a next operation. As a result of the use of the holder 25, the device 1 has a simple structure and does not need to comprise a cooling system to bring and/or maintain the water in solid state 23 at a prescribed temperature.

The second embodiment of a device 1' for treating human skin in accordance with the invention also is a device for removing hairs from human skin, in particular an epilator for removing the hairs for a relatively long time or even permanently. FIG. 2 schematically shows only the main parts of the device 1' which are necessary to understand the principles of the invention. Parts of the device 1' which correspond to parts of the device 1 shown in FIG. 1 and which were discussed in the foregoing are indicated with corresponding reference numbers in FIG. 2 and will not be discussed in detail. Hereafter only the main differences between the device 1' and the device 1 will be briefly discussed.

The device 1' mainly differs from the device 1 in that, unlike the radiation filter 17 of the device 1 comprising the first filter portion 19 and the second filter portion 21, the device 1' comprises a radiation filter 41 which is arranged in the head 7' near the front portion 11'. The radiation filter 41 comprises a holder 43 having a chamber 45 for containing water in solid state 47. The holder 43 is releasable and removable from the device 1' in the direction of the arrow B in FIG. 2. The chamber 45 is enclosed by an annular carrier 49 and by a single optically transparent cover plate 51. As a result, the chamber 45 is open at a side 53 which faces the skin during operation. Said open side 53 coincides with or even slightly protrudes from the radiation exit opening 13'. As a result, the water in solid state 47 present in the holder 43 is in direct contact with the skin to be treated during operation. Said direct contact also implies that in this embodiment the water in solid state 47 is in thermal contact with the skin to be treated during operation. As a result of said direct contact between the water in solid state 47 and the skin to be treated, a small portion of the water in solid state 47 melts during operation and forms a thin water film between the water in solid state 47 and the skin to be treated. As a result of said water film a larger portion of the radiation transmitted by the radiation filter 41 is effectively transmitted or optically coupled into the skin. Said improved transmission is a result of the fact that a good optical contact is present between the water in solid state 47 and said water film and between said water film and the surface of the skin to be treated, and also of the fact that the water in the water film has a refraction coefficient which is closer to the refraction coefficient of the skin than the refraction coefficient of air. As a result of said thermal contact between the water in solid state 47 and the skin, the water in solid state 47 also provides a skin cooling effect. Despite the filtering function of the water in solid state 47, the skin to be treated is still heated as a result of the absorption of the portion of the light which is transmitted by the radiation filter 41. In this embodiment the cooling effect of the water in solid state 47 does not only limit or prevent heating of the skin, but also provides a pain masking effect. Said pain masking effect is obtained as a result of the fact that nerve stimuli, which are caused by and associated with the cooling of the skin, limit or block the transmission of nerve stimuli associated with possible pain experienced as a result of the treatment of the skin.

As shown in FIG. 2 the holder 43 of the device 1' is arranged in a cylindrical recess 55 provided in the front portion 11' of the head 7'. The holder 43 comprises positioning means 57 which define a predetermined position of the holder 43 and the water in solid state 47 relative to the device 1' and the radiation path 15'. In the embodiment shown said positioning means 57 are formed by a circumferential edge portion of the annular carrier 49, which matches the recess 55.

In the device 1' the cover plate 51 of the holder 43 is made from an optically transparent material which has an optical transmission spectrum such that the cover plate 51 substantially absorbs the portion of the light generated by the radiation source 9' having wavelengths below approximately 400 nm, i.e. the UV light, and substantially transmits the portion of the light having wavelengths above approximately 400 nm. In the embodiment shown the cover plate 51 is made from a so-called optical plastic, in this example an acrylic plastic, which has a very good mechanical stability and is also known for its very good clarity and excellent transmission properties throughout the visible portion of the spectrum. An example of a commercially available acrylic plastic suitable for this purpose is ACRYLITE® H15-363 or S10-453 from CYRO Industries, Rockaway, N.J., USA. Other examples of such an optical plastic, which could be used instead, are compounds comprising polystyrene or polycarbonate. As the cover plate 51 functions as an effective UV filter, the device 1' does not need a separate UV filter such as the first filter portion 19 of the device 1 described before. In view of this double function of the cover plate 51 of the holder 43, the holder 43 is used in a practical manner, and the device 1' has a relatively simple and practical structure.

Another aspect of the device 1' shown in FIG. 2 is that the water in solid state 47 comprises an additive. As during operation of the device 1' a water film is formed on the skin to be treated, said additive is applied to the skin via the water film. In the embodiment of FIG. 2 said additive is an additive having a skin hydrating effect, such an additive being known for example as an ingredient in cosmetic creams. Instead of or in addition to such an additive, other additives may be used such as, for example, an anti-inflammatory agent for reducing visual skin irritation that may result from a light treatment of the skin, or an aneasthetic substance to desensitize the skin. In the embodiment of FIG. 2 it is further advantageous to add a thickening agent to the water in solid state 47. As a result of such a thickening agent the water will become gel-like when melting. This avoids dripping of the water out of the holder 43. Another example of a useful additive is an additive which increases the radiation absorbing capacity of the water in solid state 47 for wavelengths which are not effective for the treatment of the skin and are harmful for the skin. Specific dyes can be used for this purpose, and the skilled person will be able to find suitable dyes on the basis of the desired optical transmission spectrum of the water in solid state 47. An example of a suitable commercially available dye is the Laser Dye ADS560W5 from American Dye Source, Inc., Quebec, Canada, which has good absorbing properties for wavelengths below approximately 600 nm. Another example of a suitable dye is a fluorescent dye, such as pyridine, which has the property that it absorbs radiation with a wavelength below approximately 600 nm and converts the absorbed light into light emitted at a wavelength between 600 nm and 900 nm. An example of a suitable commercially available fluorescent dye is the Laser Dye Catalog No. LDS 698 06980 from Exciton Inc., Dayton, Ohio, USA.

FIG. 3 shows an alternative holder 59 for water in solid state which can be used in the devices 1 and 1' described before instead of the holders 25 and 43. The holder 59 comprises a first central chamber 61 in which water in solid state 63 is to be held at least during an initial phase of operation of the device 1, 1'. The first chamber 61 is surrounded by a second additional chamber 65, a heat conducting metal wall 67 made from, for example, copper being arranged between the first chamber 61 and the second chamber 65. The first chamber 61 is further enclosed by a first optically transparent cover plate 69 and by a second optically transparent cover plate 71. The second chamber 65 contains a compound 73 having a eutectic composition with a eutectic temperature which is substantially lower than the melting temperature of the water in solid state 63. A person skilled in the art will be able to find any suitable commercially available compound having a eutectic temperature between approximately −2° C. and −18° C. An example is a composition of 53% water and 47% $AgNO_3$ (mass ratios) which has a eutectic temperature of −7.3° C. Via said heat conducting metal wall 67 said compound 73 present in the second chamber 65 is in thermal contact with the water in solid state 63 present in the first chamber 61. The thermal contact between the first and second chamber 61, 65 is further improved by a plurality of parallel metal plates 75 which, in an operational position of the holder 59 in the device 1, 1', extend throughout the first and second chamber 61, 65 in a direction parallel to the radiation path 15, 15'. During operation the second chamber 65 comprising the compound 73 acts as a cooling device for cooling the water in solid state 63, i.e. at least for reducing the rate at which the temperature of the water in solid state 63 rises during operation. Before use of the device 1, 1', the holder 59 has to be placed in a freezer, so that both the water 63 and the compound 73 are brought into solid state. After placing the holder 59 in the device 1, 1', the device 1, 1' is ready for use. After a certain period of operation of the device 1, 1', the temperature of the water in solid state 63 and of the compound 73 will reach the eutectic temperature of the compound 73. From this moment on the compound 73 will melt at a substantially constant temperature below the melting temperature of the water in solid state 63, so that also the water in solid state 63 is held at said constant temperature. The melting process of the compound 73 requires a considerable amount of energy, so that the heat absorbing capacity of the water in solid state 63 is considerably increased. When the melting process of the compound 73 is finished the temperature of the water in solid state 63 rises further until the melting temperature of the water in solid state 63 is reached. From this moment on the water in solid state 63 will melt at a substantially constant temperature, for which melting process also a considerable amount of energy is necessary. It is noted that, instead of or in addition to the second chamber 65 comprising the compound 73, the device 1, 1' may comprise a different kind of cooling device for cooling the water in solid state in order to hold the water in solid state at a constant temperature or to limit the rate at which the temperature of the water in solid state increases during operation. Such a cooling device may be of a relatively simple kind. An example of a suitable cooling device with a simple structure is a thermo-electric cooler, in particular a Peltier cooler.

The embodiments of a device 1, 1' for treating human skin in accordance with the invention shown in FIGS. 1 and 2 and described herebefore are devices for removing hairs from human skin, in particular epilators for removing the hairs for a relatively long time or even permanently. It is noted, however, that the invention also includes other types of devices for treating human skin by means of radiation. Examples of such devices are devices for the medical or cosmetic treatment by means of radiation or radiation pulses of birthmarks present on the skin, such as naevus vinosus and naevus pigmentosus, psoriasis, or aberrations of blood vessels present in the skin, such as varicose veins.

It is further noted that the invention also includes embodiments in which the water in solid state is in thermal contact with the skin to be treated but not in direct contact with the skin to be treated. Such an embodiment is for example achieved by providing the holder 43 of the device 1' shown in FIG. 2 with an additional optically transparent cover plate between the water in solid state and the radiation exit opening. In such an alternative embodiment the water in solid state has a combined filtering and skin cooling effect but not a skin moistening effect.

It is further noted that the invention also includes embodiments in which the radiation exit opening is not provided in the housing accommodating the radiation source, like in the devices 1 and 1' shown in the figures, but is provided in a separate handpiece which is optically coupled with the housing accommodating the radiation source by means of, for example, an optical fiber. In such an alternative embodiment the radiation filter may be provided in said housing, but may also be provided in said handpiece.

It is further noted that a device for treating human skin according to the invention may be provided with a sensor for detecting the presence of the radiation source in the device. In such an embodiment the sensor co-operates with an electric circuit which prevents the radiation source from being activated when the sensor does not detect the presence of the radiation filter in the device.

It is finally noted that the invention comprehends both embodiments in which a releasable and removable holder for containing the water in solid state is used and embodiments in which the water in solid state is kept in a fixed holder or chamber in the device. In the case of a fixed holder the device may be provided with a cooling system for bringing and maintaining the water at a prescribed temperature. In the case of a releasable and removable holder such a holder may be designed for repetitive use or for one-off use.

The invention claimed is:

1. A device for treating human skin by means of radiation, which device comprises a housing, a radiation source accommodated in the housing, a radiation exit opening, a radiation path between the radiation source and the radiation exit opening, and a radiation filter positioned in the radiation path and comprising water, characterized in that a radiation filter positioned in the radiation path and adapted to absorb radiation of a wavelength above a first threshold value and to substantially reflect or absorb radiation of a wavelength below a second threshold value.

2. A device as claimed in claim 1, characterized in that during operation the water in solid state is in thermal contact with the skin to be treated.

3. A device as claimed in claim 1, characterized in that the device comprises a releasable and removable holder for the water in solid state.

4. A device as claimed in claim 1, wherein the radiation filter comprises water in a solid state at least during an initial phase of operation of the device.

5. A device as claimed in claim 1, characterized in that the device comprises a cooling device for cooling the water in solid state.

6. A device as claimed in claim 1, characterized in that during operation the water in solid state is in direct contact with the skin to be treated.

7. A device as claimed in claim 1, characterized in that the water in solid state comprises an additive.

8. A device as claimed in claim 1, characterized in that the device is a device for removing hairs from human skin, wherein the radiation source is a flash lamp.

9. A holder for water in solid state for use in a device as claimed in claim 3, characterized in that the holder comprises a chamber for containing water in solid state, said chamber comprising an optically transparent radiation path which, during operation, extends through the water in solid state, and said holder comprising positioning means which are arranged outside said radiation path and which define a predetermined position of said radiation path in the device.

10. A holder as claimed in claim 9, characterized in that the holder comprises an additional chamber which is in thermal contact with the chamber for containing the water in solid state and which comprises a compound having a eutectic composition with a eutectic temperature lower than the melting temperature of the water in solid state.

11. A device for treating human skin, comprising:
a radiation source accommodated in a housing;
a radiation exit opening;
a radiation path between the radiation source and the radiation exit opening; and
a radiation filter positioned in the radiation path and adapted to absorb radiation of a wavelength above a first threshold value and to substantially reflect or absorb radiation of a wavelength below a second threshold value.

12. A device as claimed in claim 11, wherein the filter comprises a first portion adapted to absorb the radiation above the first threshold value and a second portion adapted to substantially reflect or absorb the radiation below the second threshold value.

13. A device as claimed in claim 12, wherein the radiation filter comprises water in a solid state at least during an initial phase of operation of the device.

14. A device as claimed in claim 11, wherein the first threshold is approximately 900 nm and the second threshold is approximately 600 nm.

15. A device as claimed in claim 13, wherein the first filter portion includes the water.

16. A device as claimed in claim 11, wherein the second threshold is approximately 400 nm.

* * * * *